United States Patent [19]
Nesvadba et al.

[11] Patent Number: 5,807,505
[45] Date of Patent: Sep. 15, 1998

[54] BENZOFURAN-2-ONES AS STABILIZERS

[75] Inventors: Peter Nesvadba; Samuel Evans, both of Marly, Switzerland

[73] Assignee: Ciba Specialty Chemicals Corporation, Tarrytown, N.Y.

[21] Appl. No.: 881,977

[22] Filed: Jun. 25, 1997

Related U.S. Application Data

[62] Division of Ser. No. 715,057, Sep. 17, 1996, Pat. No. 5,693,829, which is a division of Ser. No. 304,470, Sep. 12, 1994, Pat. No. 5,614,572.

[30] Foreign Application Priority Data

Sep. 17, 1993 [CH] Switzerland ............ 2811 93-9

[51] Int. Cl.$^6$ ............ C09K 15/04; C09K 15/06; C08K 5/15
[52] U.S. Cl. ............ 252/406; 252/399; 252/407; 524/107; 524/111
[58] Field of Search .......... 252/380, 406, 252/407, 186.25, 399; 524/111, 107, 109; 549/60, 3.7, 310; 548/440

[56] References Cited

U.S. PATENT DOCUMENTS

| | | | |
|---|---|---|---|
| 5,356,966 | 10/1994 | Nesvadba | 524/111 |
| 5,516,920 | 5/1996 | Nesvadba et al. | 549/307 |
| 5,614,572 | 3/1997 | Nesvadba et al. | 524/111 |
| 5,693,829 | 12/1997 | Nesvadba et al. | 549/307 |

FOREIGN PATENT DOCUMENTS

| | | |
|---|---|---|
| 0415887 | 3/1991 | European Pat. Off. . |
| 4202276 | 8/1992 | Germany . |
| 2257140 | 1/1993 | United Kingdom . |
| 8001566 | 8/1980 | WIPO . |

OTHER PUBLICATIONS

Houben–Weyl, vol. VI/IC p. 1030 (1976).
Organikum, pp.186–191 (1986).
Organikum, p. 388 (1986).
Organikum, p. 402–408 (1986).
Beilstein, 18, 17 (1934).
Beilstein, E III/IV, 18 pp.154–166 (1975).
Th. Kappe et al, Monats Hefte für Chemie 99, 990–994 (1968).
J. Mowian et al. Bull Soc. Chem. FR. 1979 583.
J. Org. Chem. 57 pp. 362–366 (1992).
M. Julia et al, Bull. Soc. Chem. FR 1965 2175.
H. Sterk et al Monatshefte Für Chemie 99, 2223–2226 (1968).

*Primary Examiner*—Shean C. Wu
*Attorney, Agent, or Firm*—Luther A. R. Hall

[57] ABSTRACT

The invention relates to compounds of formula I

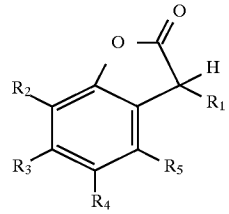

(I)

wherein the general symbols are as defined in claim 1, as stabilizers for protecting organic materials against thermal, oxidative or light-induced degradation.

4 Claims, No Drawings

BENZOFURAN-2-ONES AS STABILIZERS

This is a divisional of application Ser. No. 08/715,057, filed on Sep. 17, 1996, now U.S. Pat. No. 5,693,829, issued on Dec. 2, 1997, which is a divisional of application Ser. No. 08/304,470, filed on Sep. 12, 1994, now U.S. Pat. No. 5,614,572, issued on Mar. 25, 1997.

The present invention relates to compositions comprising an organic material, preferably a polymer, and benzofuran-2-ones as stabilisers, to the use thereof for stabilising organic materials against oxidative, thermal or light-induced degradation, and to novel benzofuran-2-ones.

Individual benzofuran-2-ones are known in the literature, and have been mentioned, inter alia, in Beilstein 18, 17 and Beilstein E III/IV, 18, 154–166, or described by Th. Kappe et al., Monatshefte für Chemie 99, 990 (1968); J. Morvan et al., Bull. Soc. Chim. Fr. 1979, 583; L. F. Clarke et al., J. Org. Chem. 57, 362 (1992); M. Julia et al., Bull. Soc. Chim. Fr. 1965, 2175, or by H. Sterk et al., Monatshefte für Chemie 99, 2223 (1968). In no publication are these compounds used as stabilisers for organic materials.

The use of some benzofuran-2-ones as stabilisers for organic polymers is disclosed, inter alia, in U.S. Pat. No. 4,325,863; U.S. Pat. No. 4,338,244 and U.S. Pat. No. 5,175,312.

It has now been found that a selected group of benzofuran-2-ones is particularly suitable for use as stabilisers for organic materials that are susceptible to oxidative, thermal or light-induced degradation.

Accordingly, the invention relates to compositions comprising a) an organic material that is subject to oxidative, thermal or light-induced degradation, and b) at least one compound of formula I

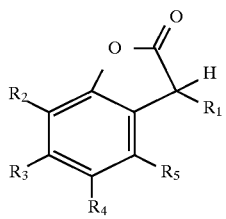

wherein $R_1$ is halogen or —$OR'_1$, $R'_1$ is hydrogen, $C_1$–$C_{25}$alkanoyl, $C_3$–$C_{25}$alkenoyl, $C_3$–$C_{25}$alkanoyl which is interrupted by oxygen, sulfur or

$C_6$–$C_9$cycloalkylcarbonyl, thenoyl, furoyl, benzoyl or $C_1$–$C_{12}$alkyl-substituted benzoyl; naphthoyl or $C_1$–$C_{12}$alkyl-substituted naphthoyl; $C_1$–$C_{25}$alkanesulfonyl, fluoro-substituted $C_1$–$C_{25}$alkanesulfonyl; phenylsulfonyl or $C_1$–$C_{12}$alkyl-substituted phenylsulfonyl;

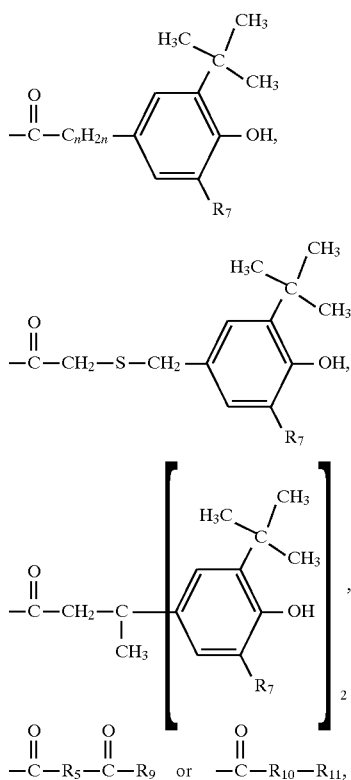

$R_2$, $R_3$, $R_4$ and $R_5$ are each independently of one another hydrogen, chloro, hydroxy, $C_1$–$C_{25}$alkyl, $C_7$–$C_9$-phenylalkyl, unsubstituted or $C_1$–$C_4$alkyl-substituted phenyl, unsubstituted or $C_1$–$C_4$alkyl-substituted $C_5$–$C_8$cycloalkyl; $C_1$–$C_{18}$alkoxy, $C_1$–$C_{18}$alkylthio, $C_1$–$C_4$alkylamino, di-($C_1$–$C_4$alkyl)amino, $C_1$–$C_{25}$alkanoyloxy, $C_1$–$C_{25}$alkanoylamino, $C_3$–$C_{25}$alkenoyloxy, $C_3$–$C_{25}$alkanoyloxy which is interrupted by oxygen, sulfur or

$C_6$–$C_9$cycloalkylcarbonyloxy, benzoyloxy or $C_1$–$C_{12}$alkyl-substituted benzoyloxy; or each pair of substituents $R_2$ and $R_3$ or $R_3$ and $R_4$ or $R_4$ and $R_5$, together with the linking carbon atoms, forms a benzene ring; $R_4$ is additionally —$(CH_2)_p$—$COR_9$ or —$(CH_2)_q$OH, or, if $R_3$ and $R_5$ are hydrogen, $R_4$ is additionally a radical of formula II

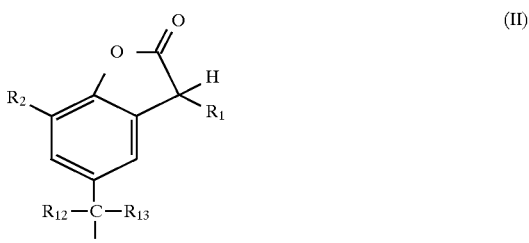

$R_6$ is hydrogen or $C_1$–$C_8$alkyl,
$R_7$ is hydrogen or $C_1$–$C_8$alkyl,
$R_8$ is a direct bond, $C_1$–$C_{18}$alkylene, $C_2$–$C_{18}$alkylene which is interrupted by oxygen, sulfur or

$C_2$–$C_{18}$alkenylene, $C_2$–$C_{20}$alkylidene, $C_7$–$C_{20}$phenylalkylidene, $C_5$–$C_8$cycloalkylene, $C_7$–$C_8$bicycloalkylene, unsubstituted or $C_1$–$C_4$alkyl-substituted phenylene,

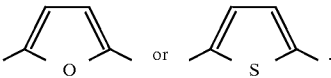

$R_9$ is hydroxy,

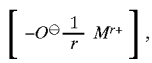

$C_1$–$C_{18}$alkoxy or

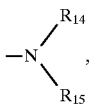

$R_{10}$ is oxygen, —NH— or

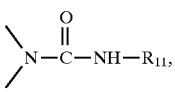

$R_{11}$ is $C_1$–$C_{18}$alkyl or phenyl,
$R_{12}$ and $R_{13}$ are each independently of the other hydrogen, $CF_3$, $C_1$–$C_{12}$alkyl or phenyl, or
$R_{12}$ and $R_{13}$, together with the linking carbon atom, form a $C_5$–$C_8$cycloalkylidene ring which is unsubstituted or substituted by 1 to 3 $C_1$–$C_4$alkyl groups,
$R_{14}$ and $R_{15}$ are each independently of the other hydrogen, or $C_1$–$C_{18}$alkyl,
M is a metal cation of valency r,
n is 0, 1 or 2,
p is 0, 1 or 2,
q is 1, 2, 3, 4, 5 or 6, and
r is 1, 2 or 3.

Halogen substituents will conveniently be chloro, bromo or iodo. Chloro is preferred.

Alkanoyl of up to 25 carbon atoms inclusive is a branched or unbranched radical, typically including formyl, acetyl, propionyl, butanoyl, pentanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, eicosanoyl or docosanoyl. $R'_1$ defined as alkanoyl preferably contains 2 to 18, most preferably 2 to 12, e.g. 2 to 6, carbon atoms. Acetyl is particularly preferred.

Alkanoyloxy of up to 25 carbon atoms inclusive is an unbranched or branched radical and is typically formyloxy, acetoxy, propionyloxy, butanoyloxy, pentanoyloxy, hexanoyloxy, heptanoyloxy, octanoyloxy, nonanoyloxy, decanoyloxy, undecanoyloxy, dodecanoyloxy, tridecanoyloxy, tetradecanoyloxy, pentadecanoyloxy, hexadecanoyloxy, heptadecanoyloxy, octadecanoyloxy, eicosanoyloxy or docosanoyloxy. Alkanoyloxy of 2 to 18, preferably 2 to 12, e.g. 2 to 6, carbon atoms is preferred. Acetoxy is particularly preferred..

Alkenoyl of 3 to 25 carbon atoms is a branched or unbranched radical, typically including propenoyl, 2-butenoyl, 3-butenoyl, isobutenoyl, n-2,4-pentadienoyl, 3-methyl-2-butenoyl, n-2-octenoyl, n-2-dodecenoyl, isododecenoyl, oleoyl, n-2-octadecenoyl or n-4-octadecenoyl. Alkenoyl of 3 to 18, preferably 3 to 12, e.g. 3 to 6, most preferably 3 to 4, carbon atoms is preferred.

Alkenoyloxy of 3 to 25 carbon atoms is a branched or unbranched radical, typically including propenoyloxy, 2-butenoyloxy, 3-butenoyloxy, isobutenoyloxy, n-2,4-pentadienoyloxy, 3-methyl-2-butenoyloxy, n-2-octenoyloxy, n-2-dodecenoyloxy, isododecenoyloxy, oleoyloxy, n-2-octadecenoyloxy or n-4-octadecenoyloxy. Alkenoyloxy of 3 to 18, preferably 3 to 12, typically 3 to 6, most preferably 3 to 4, carbon atoms is preferred.

$C_3$–$C_{25}$Alkanoyl which is interrupted by oxygen, sulfur or >N—$R_6$, will typically be $CH_3$—O—$CH_2CO$—, $CH_3$—S—$CH_2CO$—, $CH_3$—NH—$CH_2CO$—, $CH_3$—N($CH_3$)—$CH_2CO$—, $CH_3$—O—$CH_2CH_2$—O—$CH_2CO$—, $CH_3$—(O—$CH_2CH_2$—)$_2$O—$CH_2CO$—, $CH_3$—(O—$CH_2CH_2$—)$_3$O—$CH_2CO$— or $CH_3$—(O—$CH_2CH_2$—)$_4$O—$CH_2CO$—.

$C_3$–$C_{25}$Alkanoyloxy which is interrupted by oxygen, sulfur or >N—$R_6$ will typically be $CH_3$—O—$CH_2COO$—, $CH_3$—S—$CH_2COO$—, $CH_3$—NH—$CH_2COO$—, $CH_3$—N($CH_3$)—$CH_2COO$—, $CH_3$—O—$CH_2CH_2$—O—$CH_2COO$—, $CH_3$—(O—$CH_2CH_2$—)$_2$O—$CH_2COO$—, $CH_3$—(O—$CH_2CH_2$—)$_3$O—$CH_2COO$— or $CH_3$—(O—$CH_2CH_2$—)$_4$O—$CH_2COO$—.

$C_6$–$C_9$Cycloalkylcarbonyl is typically cyclopentylcarbonyl, cyclohexylcarbonyl, cycloheptylcarbonyl or cyclooctylcarbonyl. Cyclohexylcarbonyl is preferred.

$C_6$–$C_9$Cycloalkylcarbonyloxy is typically cyclopentylcarbonyloxy, cyclohexylcarbonyloxy, cycloheptylcarbonyloxy or cyclooctylcarbonyloxy. Cyclohexylcarbonyloxy is preferred.

$C_1$–$C_{12}$Alkyl-substituted benzoyl which preferably carries 1 to 3, most preferably 1 or 2 alkyl groups, is typically o-, m- or p-methylbenzoyl, 2,3-dimethylbenzoyl, 2,4-dimethylbenzoyl, 2,5-dimethylbenzoyl, 2,6-dimethylbenzoyl, 3,4-dimethylbenzoyl, 3,5-dimethylbenzoyl, 2-methyl-6-ethylbenzoyl, 4tert-butylbenzoyl, 2-ethylbenzoyl, 2,4,6-trimethylbenzoyl, 2,6-dimethyl-4-tert-butylbenzoyl or 3,5-di-tert-butylbenzoyl. Preferred substituents are $C_1$–$C_8$alkyl, most preferably $C_1$–$C_4$alkyl.

$C_1$–$C_{12}$Alkyl-substituted benzoyloxy which preferably carries 1 to 3, most preferably 1 or 2 alkyl groups, is typically o-, m- or p-methylbenzoyloxy, 2,3-dimethylbenzoyloxy, 2,4-dimethylbenzoyloxy, 2,5-dimethylbenzoyloxy, 2,6-dimethylbenzoyloxy, 3,4-dimethylbenzoyloxy, 3,5-dimethylbenzoyloxy, 2-methyl-6-ethylbenzoyloxy, 4-tert-butylbenzoyloxy, 2-ethylbenzoyloxy, 2,4,6-trimethylbenzoyloxy, 2,6-dimethyl-4-tert-butylbenzoyloxy or 3,5-di-tert-butylbenzoyloxy. Preferred substituents are $C_1$–$C_8$alkyl, preferably $C_1$–$C_4$alkyl.

$C_1$–$C_{12}$Alkyl-substituted naphthoyl, which is 1-naphthoyl or 2-naphthoyl and preferably contains 1 to 3, most preferably 1 or 2 alkyl groups, will typically be 1-, 2-, 3-, 4-, 5-, 6-, 7- or 8-methylnaphthoyl, 1-, 2-, 3-, 4-, 5-, 6-, 7- or 8-ethylnaphthoyl, 4-tert-butylnaphthoyl or 6-tert-butylnaphthoyl. Particularly preferred substituents are $C_1$–$C_8$alkyl, most preferably $C_1$–$C_4$alkyl.

$C_1$–$C_{25}$Alkanesulfonyl is a branched or unbranched radical, typically methanesulfonyl, ethanesulfonyl, propanesulfonyl, butanesulfonyl, pentanesulfonyl, hexanesulfonyl, heptanesulfonyl, cctanesulfonyl, nonanesulfonyl or docosanesulfonyl. Alkanesulfonyl of 1 to 18, preferably 1 to 12, e.g. 2 to 6, carbon atoms is preferred. Methanesulfonyl is particularly preferred.

Fluoro-substituted $C_1$–$C_{25}$alkanesulfonyl is typically trifluoromethanesulfonyl.

$C_1$–$C_{12}$Alkyl-substituted phenylsulfonyl which carries preferably 1 to 3, most preferably 1 or 2, alkyl groups is typically o-, m- or p-methylphenylsulfonyl, p-ethylphenylsulfonyl, p-propylphenylsulfonyl or p-butylphenylsulfonyl. Preferred substituents are $C_1$–$C_8$alkyl, most preferably $C_1$–$C_4$alkyl. p-Methylphenylsulfonyl is particularly preferred.

Alkyl of up to 25 carbon atoms is a branched or unbranched radical and is typically methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, eicosyl or docosyl. A preferred meaning of $R_2$ and $R_4$ is typically $C_1$–$C_{18}$alkyl. A particularly preferred meaning of $R_4$ is $C_1$–$C_4$alkyl.

$C_7$–$C_9$Phenylalkyl may typically be benzyl, α-methylbenzyl, α,α-dimethylbenzyl or 2-phenylethyl. Benzyl and α,α-dimethylbenzyl are preferred.

$C_1$–$C_4$Alkyl-substituted phenyl that preferably contains 1 to 3, preferably 1 or 2, alkyl groups, will typically be o-, m- or p-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-methyl-6-ethylphenyl, 4-tert-butylphenyl, 2-ethylphenyl or 2,6-diethylphenyl.

Unsubstituted or $C_1$–$C_4$alkyl-substituted $C_5$–$C_8$cycloalkyl is typically cyclopentyl, methylcyclopentyl, dimethylcyclopentyl, cyclohexyl, methylcyclohexyl, dimethylcyclohexyl, trimethylcyclohexyl, tert-butylcyclohexyl, cycloheptyl or cyclooctyl. Cyclohexyl and tert-butylcyclohexyl are preferred.

Alkoxy of up to 18 carbon atoms is a branched or unbranched radical and is typically methoxy, ethoxy, propoxy, isopropoxy, n-butoxy, isobutoxy, pentoxy, isopentoxy, hexoxy, heptoxy, octoxy, decyloxy, tetradecyloxy, hexadecyloxy or octadecyloxy. Alkoxy of 1 to 12, preferably 1 to 8, e.g. 1 to 6, carbon atoms is preferred.

Alkylthio of up to 18 carbon atoms is a branched or unbranched radical and is typically methylthio, ethylthio, propylthio, isopropylthio, n-butylthio, isobutylthio, pentylthio, isopentylthio, hexylthio, heptylthio, octylthio, decylthio, tetradecylthio, hexadecylthio or octadecylthio. Alkylthio of 1 to 12, preferably 1 to 8, e.g. 1 to 6, carbon atoms is preferred.

Alkylamino of up to 4 carbon atoms is a branched or unbranched radical and is typically methylamino, ethylamino, propylamino, isopropylamino, n-butylamino, isobutylamino or tert-butylamino.

Di($C_1$–$C_4$)alkylamino also signifies that the two moieties, each independently of the other, are branched or unbranched, and is typically dimethylamino, methylethylamino, diethylamino, methyl-n-propylamino, methylisopropylamino, methyl-n-butylamino, methylisobutylamino, ethylisopropylamino, ethyl-n-butylamino, ethylisobutylamino, ethyl-tert-butylamino, diethylamino, diisopropylamino, isopropyl-n-butylamino, isopropylisobutylamino, di-n-butylamino or diisobutylamino.

Alkanoylamino of up to 25 carbon atoms is an unbranched or branched radical and is typically formylamino, acetylamino, propionylamino, butanoylamino, pentanoylamino, hexanoylamino, heptanoylamino, octanoylamino, nonanoylamino, decanoylamino, undecanoylamino, dodecanoylamino, tridecanoylamino, tetradecanoylamino, pentadecanoylamino, hexadecanoylamino, heptadecanoylamino, octadecanoylamino, eicosanoylamino oder docosanoylamino. Alkanoylamino of 2 to 18, preferably 2 to 12, e.g. 2 to 6, carbon atoms is preferred.

$C_1$–$C_{18}$Alkylene is a branched or unbranched radical, typically methylene, ethylene, propylene, trimethylene, tetramethylene, pentamethylene, hexamethylene, heptamethylene, octamethylene, decamethylene, dodecamethylene or octadecamethylene. $C_1$–$C_{12}$Alkylene is preferred, and $C_1$–$C_8$alkylene is particularly preferred.

$C_2$–$C_{18}$Alkylene which is interrupted by oxygen, sulfur or >N–$R_6$ will typically be —CH$_2$—O—CH$_2$—, —CH$_2$—S—CH$_2$—, —CH$_2$—NH—CH$_2$—, —CH$_2$—N(CH$_3$)—CH$_2$—, —CH$_2$—O—CH$_2$CH$_2$—O—CH$_2$—, —CH$_2$—(O—CH$_2$CH$_2$—)$_2$O—CH$_2$—, —CH$_2$—(O—CH$_2$CH$_2$—)$_3$O—CH$_2$—, —CH$_2$—(O—CH$_2$CH$_2$—)$_4$O—CH$_2$— or —CH$_2$CH$_2$—S—CH$_2$CH$_2$—.

$C_2$–$C_{18}$Alkenylene is typically vinylene, methylvinylene, octenylethylene or dodecenylethylene. $C_2$–$C_8$Alkenylene is preferred.

Alkylidene of 2 to 20 carbon atoms may typically be ethylidene, propyliden, butylidene, pentylidene, 4-methylpentylidene, heptylidene, nonylidene, tridecylidene, nonadecylidene, 1-methylethylidene, 1-ethylpropylidene or 1-ethylpentylidene. $C_2$–$C_8$Alkylidene is preferred.

Phenylalkylidene of 7 to 20 carbon atoms may typically be benzylidene, 2-phenylethylidene or 1-phenyl-2-hexylidene. $C_7$–$C_9$Phenylalkylidene is preferred.

$C_5$–$C_8$Cycloalkylene is a saturated hydrocarbon group having two free valences and at least one ring unit and is typically cyclopentylene, cyclohexylene, cycloheptylene or cyclooctylene. Cyclohexylene is preferred.

$C_7$–$C_8$Bicycloalkylene may be bicycloheptylene or bicyclooctylene.

Unsubstituted or $C_1$–$C_4$alkyl-substituted phenylene may be 1,2-, 1,3- or 1,4-phenylene.

A $C_1$–$C_4$alkyl-substituted $C_5$–$C_8$cycloalkylidene ring that preferably contains 1 to 3, most preferably 1 or 2, branched or unbranched alkyl groups, is typically cyclopentylidene, methylcyclopentylidene, dimethylcyclopentylidene, cyclohexylidene, methylcyclohexylidene, dimethylcyclohexylidene, trimethylcyclohexylidene, tert-butylcyclohexylidene, cycloheptylidene or cyclooctylidene. Cyclohexylidene and tert-butylcyclohexylidene are preferred.

A mono-, di- or trivalent metal cation is preferably an alkali metal cation, an alkaline earth metal cation or an aluminium cation, typically Na$^+$, K$^+$, Mg$^{++}$, Ca$^{++}$ or Al$^{+++}$.

Interesting compositions are those comprising compounds of formula I, wherein $R'_1$ is hydrogen, $C_1$–$C_{18}$alkanoyl, $C_3$–$C_{18}$alkenoyl, $C_3$–$C_{18}$alkanoyl which is interrupted by oxygen, sulfur or

$C_6$–$C_8$cycloalkylcarbonyl, thenoyl, furoyl, benzoyl or $C_1$–$C_{18}$alkyl-substituted benzoyl; naphthoyl or $C_1$–$C_8$alkyl-substituted naphthoyl; $C_1$–$C_8$alkanesulfonyl, fluoro-substituted $C_1$–$C_{18}$alkanesulfonyl; phenylsulfonyl or $C_1$–$C_8$alkyl-substituted phenylsulfonyl;

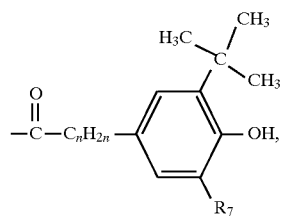

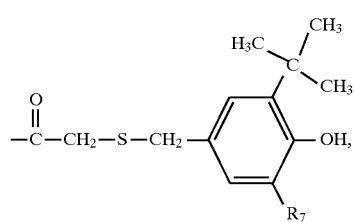

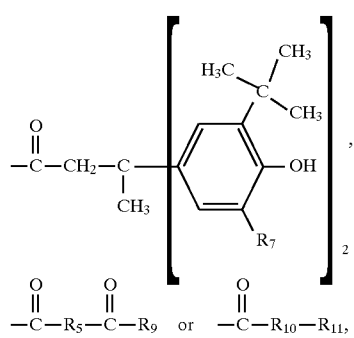

$R_2$, $R_3$, $R_4$ and $R_5$ are each independently of one another hydrogen, chloro, hydroxy, $C_1$–$C_{25}$alkyl, $C_7$–$C_9$phenylalkyl, unsubstituted or $C_1$–$C_4$alkyl-substituted phenyl, unsubstituted or $C_1$–$C_4$alkyl-substituted $C_5$–$C_8$cycloalkyl; $C_1$–$C_{12}$alkoxy, $C_1$–$C_{12}$alkylthio, $C_1$–$C_4$alkylamino, di($C_1$–$C_4$alkyl)amino, $C_1$–$C_{18}$alkanoyloxy, $C_1$–$C_{18}$alkanoylamino, $C_3$–$C_{18}$alkenoyloxy, $C_3$–$C_{18}$alkanoyloxy which is interrupted by oxygen, sulfur or

$C_6$–$C_8$cycloalkylcarbonyloxy, benzoyloxy or $C_1$–$C_8$alkyl-substituted benzoyloxy, or each pair of substituents $R_2$ and $R_3$ or $R_3$ and $R_4$ or $R_4$ and $R_5$, together with the linking carbon atoms, forms a benzene ring; $R_4$ is aditionally —$(CH_2)_p$—$COR_9$ or —$(CH_2)_q$OH; or, if $R_3$ and $R_5$ are hydrogen, $R_4$ is additionally a radical of formula II

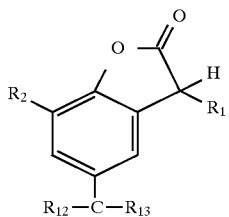

$R_6$ is hydrogen or $C_1$–$C_6$alkyl,
$R_7$ is hydrogen or $C_1$–$C_6$alkyl,
$R_8$ is a direct bond, $C_1$–$C_{12}$alkylene, $C_2$–$C_{12}$alkylene which is interrupted by oxygen, sulfur or

$C_2$–$C_{12}$alkenylene, $C_2$–$C_{12}$alkylidene, $C_7$–$C_{12}$phenylalkylidene, $C_5$–$C_8$cycloalkylene, $C_7$–$C_8$bicycloalkylene or phenylene,
$R_9$ is hydroxy, $C_1$–$C_{12}$alkoxy or

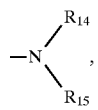

$R_{10}$ is oxygen or —NH—,
$R_{11}$ is $C_1$–$C_{12}$alkyl or phenyl,
$R_{12}$ and $R_{13}$ are methyl groups or, together with the linking carbon atom, form a $C_5$–$C_8$cycloalkylidene ring which is unsubstituted or substituted by 1 to 3 $C_1$–$C_4$alkyl groups,
$R_{14}$ and $R_{15}$ are each independently of the other hydrogen or $C_1$–$C_8$alkyl, and
q is 2, 3, 4, 5 or 6.

Preferred compositions are those comprising compounds of formula I, wherein at least two of the substituents $R_2$, $R_3$, $R_4$ and $R_5$ are hydrogen.

Compositions comprising compounds of formula I, wherein $R_3$ and $R_5$ are hydrogen, are also preferred.

Further preferred compounds are those comprising compounds of formula I, wherein $R_1$ is chloro, bromo or —$OR'_1$,
$R'_1$ is hydrogen, $C_1$–$C_{12}$alkanoyl, $C_3$–$C_{12}$alkanoyl which is interrupted by oxygen; cyclohexylcarbonyl, benzoyl, naphthoyl, $C_1$–$C_{12}$alkanesulfonyl, fluoro-substituted $C_1$–$C_{12}$alkanesulfonyl; phenylsulfonyl or $C_1$–$C_4$alkyl-substituted phenylsulfonyl;

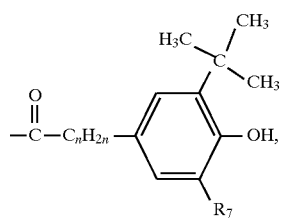

-continued $$-\overset{O}{\underset{\|}{C}}-CH_2-S-CH_2-\underset{R_7}{\underset{}{\bigcirc}}\underset{}{\overset{H_3C\diagdown\underset{|}{\overset{CH_3}{\underset{|}{C}}}\diagup CH_3}{\phantom{X}}}OH,$$

$$\left[-\overset{O}{\underset{\|}{C}}-CH_2-\underset{CH_3}{\underset{|}{C}}-\underset{R_7}{\underset{}{\bigcirc}}\underset{}{\overset{H_3C\diagdown\underset{|}{\overset{CH_3}{\underset{|}{C}}}\diagup CH_3}{\phantom{X}}}OH\right]_2,$$

$$-\overset{O}{\underset{\|}{C}}-R_5-\overset{O}{\underset{\|}{C}}-R_9 \quad \text{or} \quad -\overset{O}{\underset{\|}{C}}-R_{10}-R_{11},$$

$R_7$ is hydogen or $C_1$–$C_6$alkyl,
$R_8$ is a direct bond, $C_1$–$C_{12}$alkylene, $C_2$–$C_{12}$alkylene which is interrupted by oxygen, sulfur or $$\diagdown_{N-R_6;}\diagup$$

$C_2$–$C_{12}$alkenylene, $C_2$–$C_{12}$alkylidene, $C_7$–$C_{12}$phenylalkylidene, $C_5$–$C_8$cycloalkylene, $C_7$–$C_8$bicycloalkylene or phenylene,
$R_9$ is hydroxy, $C_1$–$C_{12}$alkoxy or $$-N\diagdown_{R_{15}}^{R_{14}},$$

$R_{10}$ is oxygen or —NH—,
$R_{11}$ is $C_1$–$C_{12}$alkyl or phenyl, and
$R_{14}$ and $R_{15}$ are each independently of the other hydrogen or $C_1$–$C_8$alkyl.

Particularly interesting compositions are those comprising compounds of formula I, wherein $R'_1$ is hydrogen, $C_1$–$C_8$alkanoyl, benzoyl, methanesulfonyl, p-methylphenylsulfonyl, $$-\overset{O}{\underset{\|}{C}}-C_nH_{2n}-\underset{R_7}{\underset{}{\bigcirc}}\underset{}{\overset{H_3C\diagdown\underset{|}{\overset{CH_3}{\underset{|}{C}}}\diagup CH_3}{\phantom{X}}}OH$$

or $$-\overset{O}{\underset{\|}{C}}-R_{10}-R_{11},$$

$R_7$ is hydrogen or $C_1$–$C_4$alkyl,
$R_{10}$ is —NH—, $R_{11}$ is $C_1$–$C_8$alkyl or phenyl, and
n is 2.

Particularly preferred compositions are those comprising compounds of formula I, wherein $R_2$, $R_3$, $R_4$ and $R_5$ are each independently of one another hydrogen, chloro, hydroxy, $C_1$–$C_{18}$alkyl, $C_7$–$C_9$phenylalkyl, phenyl, $C_5$–$C_8$cycloalkyl, $C_1$–$C_6$alkoxy, cyclohexylcarbonyloxy or benzoyloxy, or each of the pairs of substituents $R_2$ and $R_3$ or $R_3$ and $R_4$ or $R_4$ and $R_5$, together with the linking carbon atoms, forms a benzene ring; $R_4$ is additionally —(CH$_2$)$_p$—COR$_9$, or, if $R_3$ and $R_5$ are hydrogen, $R_4$ is additionally a radical of formula II,
$R_7$ is hydrogen or $C_1$–$C_4$alkyl,
$R_8$ is $C_1$–$C_{12}$alkylene or phenylene,
$R_9$ is hydroxy or $C_1$–$C_8$alkoxy,
$R_{10}$ is —NH—,
$R_{11}$ is $C_1$–$C_8$alkyl or phenyl, and
$R_{12}$ and $R_{13}$ are methyl groups or, together with the linking carbon atom, form a $C_5$–$C_8$cycloalkylidene ring.

More particularly preferred compositions are those comprising compounds of formula I wherein $R_1$ is chloro or —OR'$_1$,
$R'_1$ is hydrogen, $C_1$–$C_8$alkanoyl, benzoyl, methanesulfonyl, trifluoromethanesulfonyl, phenylsulfonyl or $C_1$–$C_4$alkyl-substituted phenylsulfonyl;

$$-\overset{O}{\underset{\|}{C}}-C_nH_{2n}-\underset{R_7}{\underset{}{\bigcirc}}\underset{}{\overset{H_3C\diagdown\underset{|}{\overset{CH_3}{\underset{|}{C}}}\diagup CH_3}{\phantom{X}}}OH$$

or $\quad -\overset{O}{\underset{\|}{C}}-R_{10}-R_{11},$ $R_2$, $R_3$, $R_4$ and $R_5$ are each independently of one another hydrogen, chloro, $C_1$–$C_{18}$alkyl, $C_7$–$C_9$phenylalkyl, phenyl, cyclohexyl, $C_1$–$C_6$alkoxy, $R_4$ is additionally —(CH$_2$)$_p$—COR$_9$, or, if $R_3$ and $R_5$ are hydrogen, $R_4$ is additionally a radical of formula II $$\underset{R_{12}-\overset{|}{\underset{|}{C}}-R_{13}}{\underset{}{\bigcirc}}\overset{R_2}{\phantom{X}}\overset{O}{\underset{}{\diagup}}\overset{O}{\underset{\|}{\diagdown}}\overset{H}{\underset{R_1}{\diagup}} \quad (II)$$

$R_7$ is hydrogen or $C_1$–$C_4$alkyl,
$R_9$ is hydroxy or $C_1$–$C_8$alkoxy,
$R_{10}$ is —NH—,
$R_{11}$ is $C_1$–$C_4$alkyl or phenyl,
$R_{12}$ and $R_{13}$, together with the linking carbon atom, form a cyclohexylidene ring,
n is 2, and
p is 2.

Very particularly preferred compositions are those comprising compounds of formula I, wherein $R_1$ is chloro or $-OR'_1$,
$R'_1$ is hydrogen, acetyl

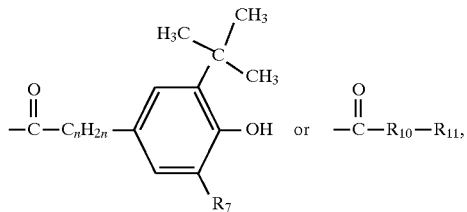

$R_2$ is $C_1$–$C_{16}$alkyl, $C_7$–$C_9$phenylalkyl or cyclohexyl,
$R_3$ is hydrogen,
$R_4$ is $C_1$–$C_4$alkyl, $C_7$–$C_9$phenylalkyl, cyclohexyl, $-CH_2CH_2COOH$ or a radical of formula II

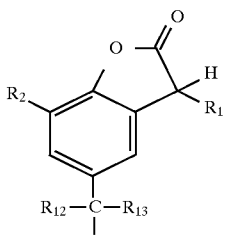

(II)

$R_5$ is hydrogen,
$R_7$ is hydrogen or $C_1$–$C_4$alkyl,
$R_{10}$ is $-NH-$,
$R_{11}$ is $C_1$–$C_4$alkyl,
$R_{12}$ and $R_{13}$, together with the linking carbon atom, form a cyclohexylidene ring, and
n is 2.

The compounds of formula I are suitable for stabilising organic materials against thermal, oxidative or light-induced degradation.

Illustrative examples of such materials are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:
 a) radical polymerisation (normally under high pressure and at elevated temperature).
 b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidenenorbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, polyisocyanates or epoxy resins.

26. Crosslinked epoxy resins derived from polyepoxides, for example from bisglycidyl ethers or from cycloaliphatic diepoxides.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrene/butadiene copolymers.

Preferred organic materials are polymers, typically naturally, semi-synthetic or, preferably, synthetic polymers, more particularly thermoplastic polymers, tackifiers or adhesives. Especially preferred organic materials are polyolefins such as polypropylene or polyethylene.

To be singled out for special mention is the efficacy of the novel compounds against thermal and oxidative degradation, especially under the action of heat which occurs during the processing of thermoplasts. The compounds of this invention are therefore admirably suited for use as processing stabilisers.

The compounds of formula I will preferably be added to the organic material to be stabilised in concentrations of 0.0005 to 5%, preferably 0.001 to 2%, typically 0.01 to 2%, based on the weight of said material.

In addition to comprising the compounds of formula I, the inventive compositions may comprise further co-stabilisers, typically the following:

1. Antioxidants
1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-($\alpha$-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.
1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.
1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.
1.4. Tocopherols, for example $\alpha$-tocopherol, $\beta$-tocopherol, $\gamma$-tocopherol, $\delta$-tocopherol and mixtures thereof (Vitamin E).
1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis-(2,6-dimethyl-4-hydroxyphenyl) disulfide.
1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4methyl-6-($\alpha$-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-($\alpha$-methylbenzyl)-4-nonylphenol], 2,2'-methylenebis[6-($\alpha,\alpha$-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy2-methylphenyl) pentane.

1.7. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tris-(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5di-tert-butyl-4-hydroxybenzylmercaptoacetate.
1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis-[4-(1,1,3,3-tetramethylbutyl)phenyl]-2,2-bis(3,5-di-tert-butyl-4-hydroxybenzyl)malonate.
1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl4-hydroxybenzyl)phenol.
1.10. Triazine Compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris-(3,5-di-tert-butyl-4-hydroxybenzyl) isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl) isocyanurate.
1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy3-methylbenzylphosphonate, the calcium salt of the monoethyl ester of 3,5-di-tert-butyl-4-hydroxybenzylphosphonic acid.
1.12. Acylaminophenols, for example 4-hydroxylauranilide, 4-hydroxystearanilide, octyl N-(3,5-di-tert-butyl-4-hydroxyphenyl)carbamate.
1.13. Esters of $\beta$-(3,5-di-tert-butyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2] octane.
1.14. Esters of $\beta$-(5-tert-butyl-4-hydroxy-3-methylphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2] octane.
1.15. Esters of $\beta$-(3,5-dicyclohexyl-4-hydroxyphenyl) propionic acid with mono- or polyhydric alcohols, e.g. with methanol, ethanol, octanol, octadecanol, 1,6- hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl) trimethylenediamine, N,N'-bis(3,5-di-tert-butyl-4-hydroxyphenylpropionyl)hydrazine.

2. UV absorbers and light stabilisers 2.1. 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-(α,α-dimethylbenzyl)-2'-hydroxyphenyl)benzotriazole, mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl) benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl)phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—$CH_2CH_2$—COO($CH_2$)$_3$—]$_2$, where R=3'-tert-butyl-4'-hydroxy-5'-2H-benzotriazol-2-ylphenyl.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutylphenyl salicylate, phenyl salicylate, octylphenyl salicylate, dibenzoyl resorcinol, bis(4-tert-butylbenzoyl) resorcinol, benzoyl resorcinol, 2,4-di-tertbutylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-piperidyl)sebacate, bis(2,2,6,6-tetramethyl-piperidyl)succinate, bis(1,2,2,6,6-pentamethylpiperidyl) sebacate, bis(1,2,2,6,6-pentamethylpiperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, the condensate of N,N'-bis(2,2,6,6-tetramethyl-4-piperidyl) hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butane-tetracarboxylate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazasprio[4.5]decan-2,4-dion, bis(1-octyloxy-2,2,6,6-tetramethylpiperidyl)sebacate, bis(1-octyloxy-2,2,6,6-tetramethylpiperidyl)succinate, the condensate of N,N'-bis-(2,2,6,6-tetramethyl-4-piperidyl) hexamethylenediamine and 4-morpholino-2,6-dichloro-1,3,5-triazine, the condensate of 2-chloro-4,6-bis(4n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl)pyrrolidine-2,5-dione.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide and mixtures of ortho- and para-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4- dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphsophite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl)methylphosphite, bis(2,4-di-tert-butyl-6-methylphenyl)ethylphosphite.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilisers, for example, copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or tin pyrocatecholate.

8. Nucleating agents, for example, 4-tert-butylbenzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxides, carbon black, graphite.

10. Other additives, for example, plasticisers, lubricants, emulsifiers, pigments, optical brighteners, flameproofing agents, antistatic agents and blowing agents.

The co-stabilisers are typically used in concentrations of 0.01 to 10%, based on the total weight of the material to be stabilised.

Further preferred compositions comprise, in addition to component (a) and the compounds of formula I, yet further additives, preferably phenolic antioxidants, light stabilisers and/or processing stabilisers.

Particularly preferred additives are phenolic antioxidants (item 1 of the list), sterically hindered amines (item 2.6 of the list), phosphites and phosphonites (item 4 of the list) and peroxide scavengers (item 5 of the list).

The compounds of formula I and other optional additives are incorporated into the organic polymer by known methods, conveniently before or during shaping to moulded articles or alternatively by coating the organic polymers with a solution or dispersion of the compounds and subsequently evaporating the solvent. The compounds of formula (1) can also be added to the materials to be stabilised in the form of a masterbatch which contains these compounds, typically in a concentration of 2.5 to 25% by weight.

The compounds of formula I can also be added before or during polymerisation or before crosslinking.

The compounds of formula I can be incorporated into the organic polymer in pure form or in waxes, oils or polymer encapsulations.

The compounds of formula I can also be sprayed on to the polymer to be stabilised. They are able to dilute other additives (typically the conventional additives listed above) or melts thereof, so that they can also be sprayed together with these additives on to the polymer to be stabilised. Application by spraying during deactivation of the polymerisation catalysts is especially advantageous, in which case spraying is conveniently effected with the vapour used for deactivation.

It may be expedient to spray the compounds of formula I, with or without other additives, on to spherical polymerised polyolefins.

The stabilised materials may be in any form of presentation, typically sheets, filaments, ribbons, mouldings, profiles or binders for coating compositions, adhesives or putties.

The invention also relates to a process for stabilising an organic material against oxidative, thermal or light-induced degradation, which comprises incorporating therein or applying thereto at least one compound of formula I.

As already emphasised, the novel compounds are used with particular advantage as stabilisers in polyolefins, preferably as heat stabilisers. Excellent stabilisation is achieved when the compounds are used in conjunction with organic phosphites or phosphonites. The novel compounds have in this case the advantage that they are effective in exceedingly low concentration, typically of 0.0001 to 0.050% by weight, preferably of 0.0001 to 0.015% by weight, based on the polyolefin. The organic phosphite or phosphonite is conveniently used in a concentration of 0.01 to 2% by weight, preferably of 0.01 to 1% by weight, based on the polyolefin. It is preferred to use the organic phosphites and phosphonites disclosed in DE-A-4 202 276. Attention is drawn in particular to the claims, to the Examples and to pages 5, last paragraph, to 8. Particularly suitable phosphites and phosphonites will also be found under item 4 of the above list of co-stabilisers.

A particularly excellent stabilisation of polyolefins is obtained by using the novel compounds in triple combination with organic phosphites or phosphonites and a phenolic antioxidant.

The invention further relates to novel compounds of formula Ia

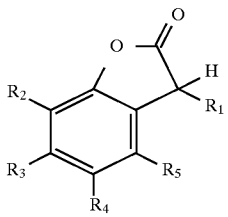

(Ia)

wherein $R_1$ is halogen or $-OR'_1$, $R'_1$ is hydrogen, $C_1-C_{25}$alkanoyl, $C_3-C_{25}$alkenoyl, $C_3-C_{25}$alkanoyl which is interrupted by oxygen, sulfur or

$C_6-C_9$cycloalkylcarbonyl, thenoyl, furoyl, benzoyl or $C_1-C_{12}$alkyl-substituted benzoyl; naphthoyl or $C_1-C_{12}$alkyl-substituted naphthoyl; $C_1-C_{25}$alkanesulfonyl, fluoro-substituted $C_1-C_{25}$alkanesulfonyl; phenylsulfonyl or $C_1-C_{12}$alkyl-substituted phenylsulfonyl;

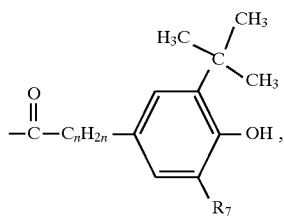

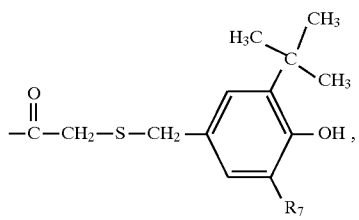

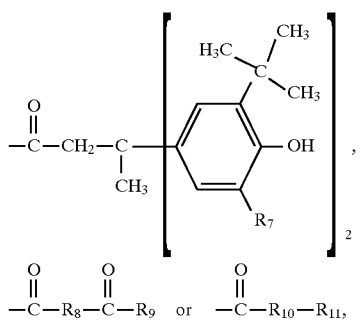

$R_2$, $R_3$, $R_4$ and $R_5$ are each independently of one another hydrogen, chloro, hydroxy, $C_1-C_{25}$alkyl, $C_7-C_9$-phenylalkyl, unsubstituted or $C_1-C_4$alkyl-substituted phenyl, unsubstituted or $C_1-C_4$alkyl-substituted $C_5-C_8$cycloalkyl; $C_1-C_{18}$alkoxy, $C_1-C_{18}$alkylthio, $C_1-C_4$alkylamino, di-$(C_1-C_4$alkyl)amino, $C_1-C_{25}$alkanoyloxy, $C_1-C_{25}$alkanoylamino, $C_3-C_{25}$alkenoyloxy, $C_3-C_{25}$alkanoyloxy which is interrupted by oxygen, sulfur or $>N-R_6$; $C_6-C_9$cycloalkylcarbonyloxy, benzoyloxy or $C_1-C_{12}$alkyl-substituted benzoyloxy; or each of the substituent pairs $R_2$ and $R_3$ or $R_3$ and $R_4$ or $R_4$ and $R_5$, together with the linking carbon atoms, forms a benzene ring; with the proviso that at least one of $R_2$, $R_3$, $R_3$, $R_4$ or $R_5$ is not hydrogen; if $R_1$ is halogen or hydroxy, $R_2$ is not hydrogen; and, if $R_2$ is methyl or methylamine, $R_4$ is not hydrogen and hydroxy; $R_4$ is additionally $-(CH_2)_p-COR_9$ or $-(CH_2)_q OH$, or, if $R_3$ and $R_5$ are hydrogen, $R_4$ is additionally a radical of formula IIa

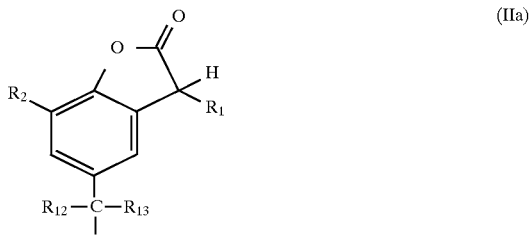

(IIa)

$R_6$ is hydrogen or $C_1-C_8$alkyl,
$R_7$ is hydrogen or $C_1-C_8$alkyl,
$R_8$ is a direct bond, $C_1-C_{18}$alkylen, $C_2-C_{18}$alkylene which is interrupted by oxygen, sulfur or

$C_2-C_{18}$alkenylene, $C_2-C_{20}$alkylidene, $C_7-C_{20}$phenylalkylidene, $C_5-C_8$cycloalkylene, $C_7-C_8$bicycloalkylene, unsubstituted or $C_1-C_4$alkyl-substituted phenylene,

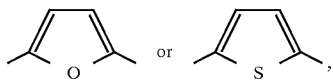

$R_9$ is hydroxy, $$\left[-O^{\ominus} \frac{1}{r} M^{r+}\right],$$

$C_1-C_{18}$alkoxy or

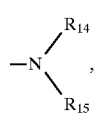

$R_{10}$ is oxygen, $-NH-$ or

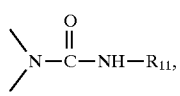

$R_{11}$ is $C_1-C_{18}$alkyl or phenyl,
$R_{12}$ and $R_{13}$ are each independently of the other hydrogen, $CF_3$, $C_1-C_{12}$alkyl or phenyl, or
$R_{12}$ and $R_{13}$, together with the linking carbon atom, form a $C_5-C_8$cycloalkylidene ring which is unsubstituted or substituted by 1 to 3 $C_1-C_4$alkyl groups,
$R_{14}$ and $R_{15}$ are each independently of the other hydrogen, or $C_1-C_{18}$alkyl,
M is a metal cation of valency r,
n is 0, 1 or 2, p is 0, 1 or 2,
q is 1, 2, 3, 4, 5 or 6, and
r is 1, 2 or 3.

Preferred groups of novel compounds of formula Ia correspond to the preferred meanings stated above in connection with the novel compositions.

Compounds of formula Ia, wherein $R_3$ and $R_5$ are hydrogen, are also preferred.

Particularly preferred compounds of formula Ia are those wherein $R_1$ is chloro, bromo or —OR'$_1$,
R'$_1$ is hydrogen, $C_1$–$C_{12}$alkanoyl, $C_3$–$C_{12}$alkanoyl which is interrupted by oxygen; cyclohexylcarbonyl, benzoyl, naphthoyl, $C_1$–$C_{12}$alkanesulfonyl, fluoro-substituted $C_1$–$C_{12}$alkanesulfonyl; phenylsulfonyl or $C_1$–$C_4$alkyl-substituted phenylsulfonyl;

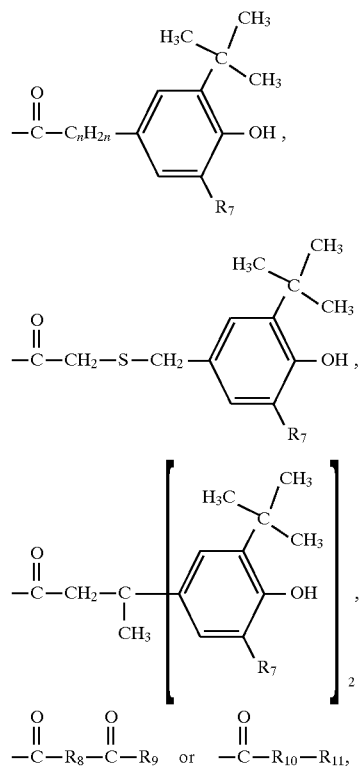

$R_2$, $R_3$, $R_4$ and $R_5$ are each independently of one another hydrogen, chloro, hydroxy, $C_1$–$C_{18}$alkyl, $C_7$–$C_9$phenylalkyl, phenyl, $C_5$–$C_8$cycloalkyl, $C_1$–$C_6$alkoxy, cyclohexylcarbonyloxy or benzoyloxy, or each of the substituent pairs $R_2$ and $R_3$ or $R_3$ and $R_4$ or $R_4$ and $R_5$, together with the linking carbon atoms, forms a benzene ring; with the proviso that at least one of $R_2$, $R_3$, $R_4$ and $R_5$ is not hydrogen; if $R_1$ is hydroxy, chloro or bromo, $R_2$ is not hydrogen; and, if $R_2$ is methyl or hydroxy, $R_4$ is not hydrogen and hydroxy; $R_4$ is additionally —(CH$_2$)$_p$—COR$_9$; or, if $R_3$ and $R_5$ are hydrogen, $R_4$ is additionally a radical of formula IIa,

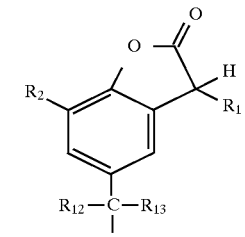

$R_7$ is hydogen or $C_1$–$C_6$alkyl,
$R_8$ is $C_1$–$C_{12}$alkylene or phenylene,
$R_9$ is hydroxy or $C_1$–$C_8$alkoxy,
$R_{10}$ is —NH—,
$R_{11}$ is $C_1$–$C_8$alkyl or phenyl, and
$R_{12}$ and $R_{13}$, together with the linking carbon atom, form a $C_5$–$C_8$cycloalkylidene ring.

Particularly preferred compounds of formula Ia are those wherein $R_1$ is chloro or —OR'$_1$,
R'$_1$ is hydrogen, $C_1$–$C_8$alkanoyl, benzoyl, methanesulfonyl, trifluoromethanesulfonyl; phenylsulfonyl or $C_1$–$C_4$alkyl-substituted phenylsulfonyl;

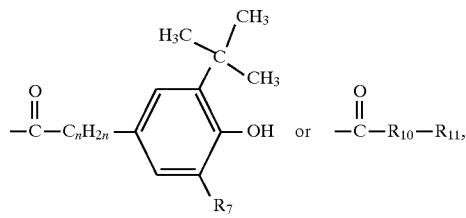

$R_2$, $R_3$, $R_4$ and $R_5$ are each independently of one another hydrogen, chloro, $C_1$–$C_{18}$alkyl, $C_7$–$C_9$phenylalkyl, phenyl, cyclohexyl, $C_1$–$C_6$alkoxy; with the proviso that at least one of $R_2$, $R_3$, $R_4$ or $R_5$ is not hydrogen; if $R_1$ is hydroxy or chloro, $R_2$ is not hydrogen; and if $R_2$ is methyl, $R_4$ is not hydrogen; $R_4$ is additionally —(CH$_2$)$_p$—COR$_9$, or, if $R_3$ and $R_5$ are hydrogen, $R_4$ is additionally a radical of formula IIa,

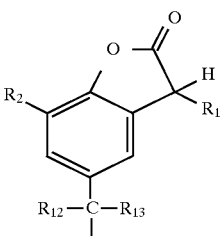

$R_7$ is hydrogen or $C_1$–$C_4$alkyl,
$R_9$ is hydroxy or $C_1$–$C_8$alkoxy,
$R_{10}$ is —NH—,
$R_{11}$ is $C_1$–$C_4$alkyl or phenyl,
$R_{12}$ and $R_{13}$, together with the linking carbon atom, form a cyclohexylidene ring,
n is 2, and
p is 2.

The compounds of formula I and formula Ia, wherein R'$_1$ is hydrogen, can be obtained in their tautomeric forms of formula Ib or formula Ic

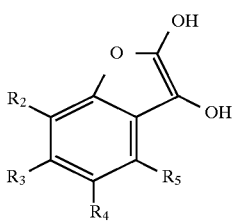

(Ib)

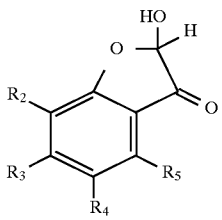

(Ic)

as described by H. Sterk et al., Monatshefte für Chemie 99, 2223 (1968). Within the scope of this application, formulae I and Ia are always to be understood as also embracing the two tautomeric formulae Ib and Ic.

The novel compounds of formula I can be prepared in per se known manner by methods analogous to literature methods described at the outset.

These known methods are somewhat troublesome and some require reagants that are expensive and, from the ecological standpoint, not entirely safe, for example selenium dioxide.

Hence the invention also relates to a novel process for the preparation of compounds of formula I, which comprises reacting a) one equivalent of a phenol of formula III

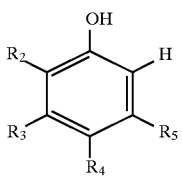

(III)

wherein the general symbols are as defined for formula I, with 0.8 to 2.0 equivalents, preferably with 0.8 to 1.2 equivalents, of glyoxylic acid, to a compound of formula IV

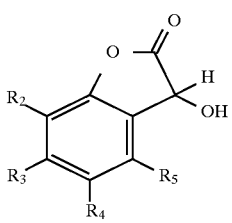

(IV)

wherein the general symbols are as defined for formula I, and b) to prepare compounds of formula I, wherein $R'_1$ is not hydrogen, reacting the resultant compound of formula IV with a hydrohalic acid, a halide of an oxysulfuric acid, a halide of phosphoric acid, a halide of phosphorous acid, with an acid of formula V $$R'_1\text{—OH} \tag{V}$$

an acid halide of formula VI $$R'_1\text{-Y} \tag{VI}$$

an ester of formula VII $$R'_1\text{—O—}R_{16} \tag{VII}$$

a symmetrical or unsymmetrical anhydride of formula VIII $$R'_1\text{—O—}R'_1 \tag{VIII}$$

or an isocyanate of formula IX $$R_{11}\text{—N═C═O} \tag{IX}$$

wherein $R'_1$ and $R_{11}$ are as defined above, with the proviso that $R'_1$ in the compounds of formulae V, VI VII and VIII are not hydrogen;
$R_{16}$ is $C_1$–$C_8$alkyl, and
Y is fluoro, chloro, bromo or iodo.

The glyoxylic acid can be used either in crystalline form or, conveniently, in the form of a commercial solution, usually a 40 to 60% aqueous solution.

A particularly interesting process for the preparation of compounds of formula IV therefore comprises using the glyoxylic acid in the form of a 40 to 60% aqueous solution, preferably of 50% aqueous glyoxylic acid.

The water present in the glyoxylic acid and the water of reaction is removed by distillation during the reaction, conveniently using a solvent that forms an azeotropic mixture with water.

Suitable solvents that form an azeotropic mixture with water do not participate in the reaction and typically include hydrocarbons such as cyclohexane or methyl cyclohexane; aromatic hydrocarbons such as benzene, toluene or xylene; halogenated hydrocarbons such as 1,2-dichloroethane; or ethers such as methyl tert-butyl ether.

When carrying out the reaction of the phenol of formula III with glyoxylic acid without a solvent to give the compounds of formula IV in the melt, the water of reaction is conveniently distilled off under normal pressure, preferably under a slight vacuum.

It is preferred to carry out the reaction at elevated temperature, preferably in the range from 60° to 120° C. A particularly preferred temperature range is from 60° to 90° C.

The reaction of the phenol of formula III with glyoxylic acid is preferably carried out in the presence of a catalyst.

Suitable catalysts are protonic acids, Lewis acids, aluminium silicates, ion exchange resins, zeolites, naturally occurring sheet silicates or modified sheet silicates.

Illustrative examples of suitable protonic acids are acids of inorganic or organic salts, typically hydrochloric acid, sulfuric acid, phosphoric acid, methanesulfonic acid, p-toluenesulfonic acid, or carboxylic acids such as acetic acid. p-Toluenesulfonic acid is particularly preferred.

Illustrative examples of suitable Lewis acids are tin tetrachloride, aluminium chloride, zinc chloride or borotrifluoride etherate. Tin tetrachloride and aluminium chloride are especially preferred.

Illustrative examples of suitable aluminium silicates are those that are widely used in petrochemical industry and are also known as amorphous aluminium silicates. These compounds contain c. 10–30% of silicon monoxide and 70–90% of aluminium oxide. A particularly preferred aluminium silicate is HA-HPV® available from Ketjen (Akzo).

Illustrative examples of suitable ion exchange resins are styrene-divinylbenzene resins which additionally carry sulfonic acid groups, for example Amberlite200® and Amberlyst® available from Rohm and Haas, or Dowex 50® available from Dow Chemicals; perfluorinated ion exchange resins such as Nafion H® sold by DuPont; or other superacid ion exchange resins such as those as described by T. Yamaguchi, Applied Catalysis, 61, 1–25 (1990) or M. Hino et al., J. Chem. Soc. Chem. Commun. 1980, 851–852.

Suitable zeolites are typically those widely used in petrochemistry as cracking catalysts and known as crystalline silicon-aluminium oxides of different crystal structure. Particularly preferred zeolites are the Faujasites available from Union Carbide, for example Zeolith X®, Zeolith Y® and ultrastabile Zeolith Y®; Zeolith Beta® and Zeolith ZSM-12® available from Mobil Oil Co.; and Zeolith Mordenit® available from Norton.

Suitable naturally occurring sheet silicates are termed "acid clays" and typically include bentonites or montmorillonites, which are degraded, ground, treated with mineral acids and calcined industrially. Particularly suitable naturally occurring sheet silicates are the Fulcat® types available from Laporte Adsorbents Co., for example Fulcat 22A®, Fulcat 22B®, Fulcat 20® or Fulcat 40®; or the Fulmont® types available from Laporte Adsorbents Co., for example Fulmont XMP-3® or Fulmont XMP-4®. A particularly preferred catalyst is Fulcat 22B®. The other Fulcat® types and Fulmont® types also belong to this preferred class, because there are only minor differences between the individual types, as for example in the number of acid centres.

Modified sheet silicates are also termed "pillared clays" and are derived from the above described naturally occurring sheet silicates by additionally containing between the silicate layers oxides of e.g. zirconium, iron, zinc, nickel, chromium, cobalt or magnesium. This type of catalyst is widely used, as described in the literature, inter alia by J. Clark et al., J. Chem. Soc. Chem. Commun. 1989, 1353–1354, but is available from only a very few firms. Particularly preferred modified sheet silicates typically include Envirocat EPZ-10®, Envirocat EPZG® or Envirocat EPIC® available from Contract Chemicals.

Preferred catalysts are naturally occurring sheet silicates or modified sheet silicates.

It is preferred to carry out the reaction of the phenol of formula III with glyoxylic acid in the presence of a Fulcat® type catalyst.

The amount of catalyst is 0.01 to 5 mol %, preferably 0.1 to 1.0 mol %, based on the phenol of formula III.

The reaction conditions for process step b) for the preparation of compounds of formula I, wherein $R'_1$ is not hydrogen, starting from compounds of formula IV, are commonly known and can be chosen in general accordance with esterification procedures described in Organikum 1986, pages 186–191, page 388 and pages 402–408.

Suitable hydrohalic acids are typically hydrochloric acid, hydrobromic acid or hydriodic acid. Hydrochloric acid is preferred.

Suitable halides of an oxysulfuric acid are typically thionyl chloride, sulfuryl chloride or thionyl bromide. Thionyl chloride is preferred.

Suitable halides of phosphoric acid and phosphorous acid typically include phosphorus trichloride, phosphorus tribromide, phosphorus triiodide, phosphorus pentachloride, phosphoroxy chloride or phosphorus pentafluoride. Phosphoroxy chloride is particularly preferred.

In process step b) it is preferred to use a halide of an oxysulfuric acid such as thionyl chloride; an acid halide of formula VI; an ester of formula VII; or a symmetrical anhydride of formula VIII.

When using a halide of an oxysulfuric acid such as thionyl chloride in process step b), it is preferred to carry out the reaction of a compound of formula IV without a solvent and in the temperature range from 0° to 40° C., preferably at room temperature. The thionyl chloride is conveniently used in a 2- to 10-fold excess, preferably in a 2- to 6-fold excess, with respect to the compound of formula IV. The reaction can also be carried out in the presence of a catalyst such as dimethyl formamide.

If an acid halide of formula VI ($R'_1$-Y), wherein Y is preferably chloro or bromo, most preferably chloro, is used in process step b), it is preferred to carry out the reaction of the compound of formula IV in the presence of a solvent and a base. The base can be used in varying amounts, from catalytic through stochiometric amounts to the multiple molar excess with respect to the compound of formula IV. The hydrogen chloride formed during the reaction may be converted by the base into the chloride, which can be removed by filtration and/or washing with a suitable aqueous or solid phase, in which case a second water-immiscible solvent can also be used. The product is conveniently purified by recrystallising the residue of the organic phase, which is concentrated or evaporated to dryness.

Suitable solvents for carrying out the reaction include hydrocarbons (typically toluene, xylene, hexane, pentane or further petroleum ether fractions), halogenated hydrocarbons (typically di- or trichloromethane, 1,2-dichloroethan, 1,1,1-trichloroethane), ethers (e.g. diethyl ether, dibutyl ether or tetrahydrofuran), and also acetonitrile, dimethyl formamide, dimethyl sulfoxide or N-methylpyrrolidone.

Suitable bases include tertiary amines, e.g. trimethylamine, triethylamine, tributylamine, N,N-dimethylaniline, N,N-diethylaniline; pyridines; hydrides (e.g. lithium, sodium or potassium hydride) or alcoholates (e.g. sodium methylate).

If an ester of formula VII ($R'_1$—O—$R_{16}$), wherein $R_{16}$ is preferably $C_1$–$C_4$alkyl, most preferably methyl or ethyl, is used in process step b), it is preferred to carry out the reaction of the compound of formula IV in the presence of a solvent that forms an azeotropic mixture with alcohols. The alcohol ($R_{16}$—OH) that forms during the reaction can be removed continuously by distillation.

Suitable solvents that form an azeotropic mixture with alcohols do not participate in the reaction and typically include hydrocarbons such as cyclohexane; aromatic hydrocarbons such as benzene or toluene; halogenated hydrocarbons such as 1,2-dichloroethane; or ethers such as methyl tert-butyl ether.

The reaction can be catalysed with a minor amount of a protonic acid such as p-toluenesulfonic acid, methanesulfonic acid, sulfuric acid or hydrochloric acid; as well as of a Lewis acid such as borotrifluoride etherate or aluminium chloride.

If a symmetrical anhydride of formula VIII ($R'_1$—O—$R'_1$), wherein $R'_1$ is preferably $C_2$–$C_6$alkanoyl, preferably acetyl, is used in process step b), it is preferred to carry out the reaction with a compound of formula IV without the addition of a further solvent and in the temperature range from 20° to 200° C., e.g. the boiling temperature of the anhydride of formula VIII, preferably from 60° to 180° C.

If an isocyanate of formula IX ($R_{11}$—N=C=O) is used, it is preferred to carry out the reaction with a compound of formula IV without the addition of a further solvent and in the temperature range from 20° to 200° C., e.g. the boiling temperature of the isocyanate of formula IX, preferably from 60° to 180° C.

The reaction with an isocyanate is likewise preferably carried out in the presence of a catalyst. Preferred catalysts correspond to those referred to above previously in connection with the reaction of the phenol of formula III with glyoxylic acid.

The phenols of formula III are known or can be prepared by per se known processes.

Bisphenols of formula X

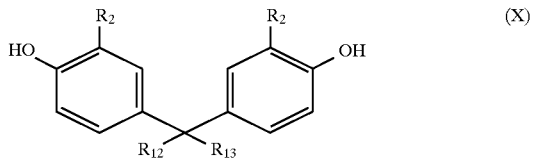

can be prepared in accordance with Houben-Weyl, Methoden der organischen Chemie, Vol. 6/1c, 1030.

The invention is illustrated in more detail by the following Examples, in which parts and percentages are by weight

EXAMPLE 1

Preparation of 5,7-di-tert-butyl-3-hydroxy-3H-benzofuran-2-one (Compound (101), Table 1)

A mixture of 21.2 g (0.10 mol) of 2,4-di-tert-butylphenol (97%), 16.3 g (0.11 mol) of 50% aqueous glyoxylic acid and 0.05 g (0.26 mmol) of p-toluenesulfonic acid monohydrate in 30 ml of 1,2-dichloroethane is refluxed under nitrogen for 3.5 hours on a water separator. Afterwards the reaction mixture is concentrated on a vacuum rotary evaporator. The residue is taken up in 80 ml of hexane and washed three times with water. The aqueous phases are separated in the separating funnel and further extracted with 30 ml of hexane. The organic phases are combined, dried over magnesium sulfate and concentrated on a vacuum rotary evaporator. The residue yields 26.23 g (~100%) of analytically pure 5,7-di-tert-butyl-3-hydroxy-3H-benzofuran-2-one in the form of a thick yellowish resin (compound (101), Table 1).

In analogy to Example 1, compounds (103), (104), (105), (109), (110) and (111) are prepared from the corresponding phenols such as 4-tert-butyl-2-methylphenol, 2,4-dicyclohexylphenol, 2-(hexadec-2-yl)-4-methylphenol, 3-[3-tert-butyl-4-hydroxyphenyl]propionic acid, 2,4-bis(α, α-dimethylbenzyl)phenol and 4-methyl-2-(1,1,3,3-tetramethylbut-1-yl)phenol with glyoxylic acid. To prepare compound (107), 2 equivalents of glyoxylic acid are used starting from 1,1-bis(3-tert-butyl-4-hydroxyphenyl) cyclohexane.

EXAMPLE 2

Preparation of 7-tert-butyl-3-hydroxy-5-methyl-3H-benzofuran-2-one (Compound (102), Table 1)

A mixture of 49.8 g (0.30 mol) of 2-tert-butyl-4-methylphenol, 48.9 g (0.33 mol) of 50% aqueous glyoxylic acid and 0.15 g (0.79 mmol) of p-toluenesulfonic acid monohydrate in 90 ml of 1,2-dichloroethane is refluxed under nitrogen for 3.5 hours on a water separator. The reaction mixture is afterwards cooled to +5° C. and the precipitate is isolated by filtration and washed with cold 1,2-dichloroethane. The filter residue is dried under a high vacuum at room temperature, affording 54.0 g (82%) of 7-tert-butyl-3-hydroxy-5-methyl-3H-benzofuran-2-one, m.p. 152°–160° C. (compound (102), Table 1).

EXAMPLE 3

Preparation of 3-acetoxy-5,7-di-tert-butyl-3H-benzofuran-2-one (compound (106), Table 1)

A mixture of 21.2 g (0.10 mol) of 2,4-di-tert-butylphenol (97%), 16.3 g (0.11 mol) of 50% aqueous glyoxylic acid and 0.05 g (0.26 mmol) of p-toluenesulfonic acid monohydrate in 30 ml of 1,2-dichloroethane is refluxed under nitrogen for 3.5 hours on a water separator. Afterwards the reaction mixture is concentrated on a vacuum rotary evaporator. The residue is taken up in 9.9 ml (0.105 mol) of acetic anhydride and the solution is refluxed for 90 minutes. The reaction mixture is then cooled to room temperature, diluted with 100 ml of tert-butyl methyl ether and washed in succession with water and dilute sodium hydrogencarbonate solution. The aqueous phases are separated and extracted with 50 ml of tert-butyl methyl ether. The organic phases are combined, dried over magnesium sulfate and concentrated on a vacuum rotary evaporator. Chromatography of the residue on silica gel with the solvent system dichloromethane/hexane=2:1 yields 28.0 g (92%) of 3-acetoxy-5,7-di-tert-butyl-3H-benzofuran-2-one (compound (106), Table 1) as a thick reddish resin.

EXAMPLE 4

Preparation of 7-tert-butyl-3-chlor-5-methyl-3H-benzofuran-2-one (Compound (108), Table 1)

To a suspension of 2.2 g (10.0 mmol) of 7-tert-butyl-3-hydroxy-5-methyl-3H-benzofuran-2-one (compound (102), Example 2, Table 1) in 2.4 ml (55.0 mmol) of thionyl chloride is added one drop of dimethyl formamide and the mixture is stirred for 2 hours at room temperature. Excess thionyl chloride is afterwards distilled off on a vacuum rotary evaporator. Chromatography of the residue on silica gel with the solvent system dichloromethane/hexane=1:1 and crystallisation of the pure fractions from methanol yields 0.30 g (13%) of 7-tert-butyl-3-chlor-5-methyl-3H-benzofuran-2-one, m.p. 81°–86° C. (compound (108), Table 1).

EXAMPLE 5

Preparation of 3-(N-methylcarbamoyloxy)-5-methyl-7-tert-butyl-3H-benzofuran-2-one (compound (112), Table 1)

A mixture of 5.5 g (25.0 mmol) of 7-tert-butyl-3-hydroxy-5-methyl-3H-benzofuran-2-one (compound (102), Example 2), 3 ml (50.0 mmol) of methyl isocyanate and 2 drops of methanesulfonic acid is refluxed for 3¼ hours. Then 3 ml (50.0 mmol) of methyl isocyanate and 2 drops of methanesulfonic acid are again added. The reaction mixture is refluxed for a further 16 hours, then cooled, diluted with dichloromethane and washed with water and 5% aqueous sodium hydrogencarbonate solution. The organic phases are combined, dried over magnesium sulfate and concentrated on a vacuum rotary evaporator. Crystallisation of the residue from toluene yields 4.45 g (65%) of 3-(N-methylcarbamoyloxy)-5-methyl-7-tert-butyl-3H-benzofuran-2-one (compound (112), Table 1), m.p. 138°–143° C.

EXAMPLE 6

Preparation of 3-[3-(3,5-di-tert-butyl-4-hydroxyphenyl)propionyloxy]-7-tert-butyl-5-methyl-3H-benzofuran-2-one (compound (113), Table 1).

A solution of 5.5 g (25.0 mmol) of 7-tert-butyl-3-hydroxy-5-methyl-3H-benzofuran-2-one (compound (102), Example 2), and 3.9 ml (28.0 mmol) of triethylamine in 30 ml of dichloromethane is added dropwise to a solution of 8.32 g (28.0 mmol) of 3-(3,5-di-tert-butyl-4-hydroxyphenyl)

propionyl chloride (prepared from 7.8 g (28.0 mmol) of 3-(3,5-di-tert-butyl-4-hydroxyphenyl)propionic acid and thionyl chloride) in 10 ml of dichloromethane. The reaction mixture is then refluxed for 1 hour, then cooled and washed with water and 5% aqueous sodium hydrogencarbonate solution. The organic phases are combined, dried over magnesium sulfate and concentrated on a vacuum rotary evaporator. Three crystallisations of the residue from acetonitrile yield 4.6 g (38%) of 3-[3-(3,5-di-tert-butyl-4-hydroxyphenyl)propionyloxy]-7-tert-butyl-5-methyl-3H-benzofuran-2-one, m.p. 151°–154° C. (compound (113), Table 1).

TABLE 1

| No. | Compound | m.p. (°C.) | C (%), H (%) (calcd/found) | Yield (%) |
|---|---|---|---|---|
| 101 | | resin | 73.25  8.45<br>73.33  8.50 | 100 |
| 102 | | 152–160 | 70.89  7.32<br>70.40  7.40 | 82 |
| 103 | | resin | characterised by<br>$^1$H-NMR (CDCl$_3$)<br>δ(H*) = 5.33 ppm | 45[a] |
| 104 | | resin | characterised by<br>$^1$H-NMR (CDCl$_3$)<br>δ(H*) = 5.30 ppm | ~100 |
| 105 | | resin | characterised by<br>$^1$H-NMR (CDCl$_3$)<br>δ(H*) = 5.31 ppm | 98 |

TABLE 1-continued

| No. | Compound | m.p. (°C.) | C (%), H (%) (calcd/found) | Yield (%) |
|---|---|---|---|---|
| 106 | | resin | 71.03  7.95<br>71.10  7.98 | 92 |
| 107 | | resin | characterised by<br>$^1$H-NMR (CDCl$_3$)<br>δ(tert-butyl) = 1.34 ppm | ~100 |
| 108 | | 81–86 | characterised by<br>$^1$H-NMR (CDCl$_3$)<br>δ(H*) = 5.34 ppm | 13 |
| 109 | | resin | characterised by<br>$^1$H-NMR (CDCl$_3$)<br>δ(H*) = 5.29 ppm | ~100 |
| 110 | | resin | characterised by<br>$^1$H-NMR (CDCl$_3$)<br>δ(H*) = 5.08 ppm | 38 |
| 111 | | 100–103 | 73.88  8.75<br>73.73  8.75 | 61 |

TABLE 1-continued

| No. | Compound | m.p. (°C.) | C (%), H (%) (calcd/found) | | Yield (%) |
|---|---|---|---|---|---|
| 112 | | 138–143 | 64.97 65.02 | 6.91 6.89 | 65 |
| 113 | | 151–154 | 74.97 74.83 | 8.39 8.38 | 38 | a)chromatographed on silica gel (CH$_2$Cl$_2$/hexane = 4:1)

EXAMPLE 7

Stabilisation of Multiple-Extruded Polypropylene 1.3 kg of polypropylene powder (Profax 6501), which has been prestabilised with 0.025% of Irganox® 1076 (n-octadecyl 3-[3,5-di-tert-butyl-4-hydroxyphenyl] propionate (melt index 3.2 g/10 min, measured at 230° C./2.16 kg) are blended with 0.05% of Irganox® 1010 (pentaerythritol tetrakis[3-(3,5-di-tert-butyl-4-hydroxyphenyl)propionate), 0.05% of calcium stearate, 0.03% of DHT 4A® (Kyowa Chemical Industry Co., Ltd., [Mg$_{4.5}$Al$_2$(OH)$_{13}$CO$_3$.3,5 H$_2$O]) and 0.05% of compound of Table 1. This blend is then extruded in an extruder having a cylinder diameter of 20 mm and a length of 400 mm at 100 rpm, the 3 heating zones being adjusted to the following temperatures: 260°, 270°, 280° C. The extrudate is cooled by drawing it through a water bath and is then granulated. This granulate is repeatedly extruded. After 3 extrusions, the melt index is measured (at 230° C./2.16 kg). A substantial increase in the melt index denotes pronounced chain degradation, i.e. poor stabilisation. The results are shown in Table 2.

TABLE 2

| Compound of Table 1 | Melt index after 3 extrusions |
|---|---|
| — | 21.3 |
| 101 | 7.1 |
| 102 | 6.6 |
| 106 | 8.4 |

What is claimed is:
1. A process for stabilizing an organic material against oxidative, thermal or light-induced degradation, which comprises incorporating therein or applying thereto at least one compound of formula I

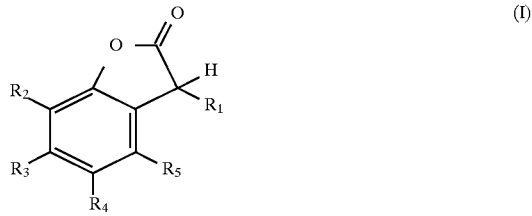

(I)

wherein

R$_1$ is halogen or —OR'$_1$,

R'$_1$ is hydrogen, C$_1$–C$_{25}$alkanoyl, C$_3$–C$_{25}$alkenoyl, C$_3$–C$_{25}$alkanoyl which is interrupted by oxygen, sulfur or >N—R$_6$; C$_6$–C$_9$cycloalkylcarbonyl, thenoyl, furoyl, benzoyl or C$_1$–C$_{12}$alkyl-substituted benzoyl; naphthoyl or C$_1$–C$_{12}$alkyl-substituted naphthoyl; C$_1$–C$_{25}$alkanesulfonyl, fluoro-substituted C$_1$–C$_{25}$alkanesulfonyl; phenylsulfonyl or C$_1$–C$_{12}$alkyl-substituted phenylsulfonyl;

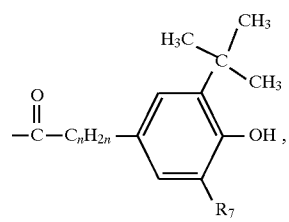

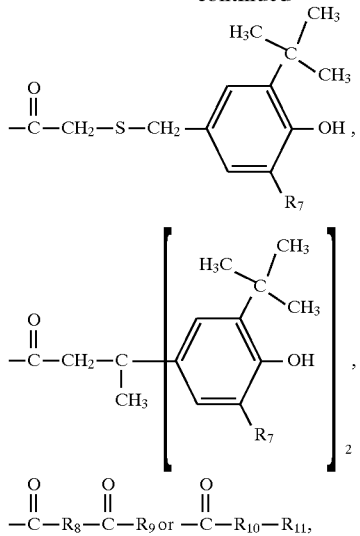

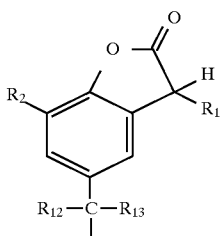

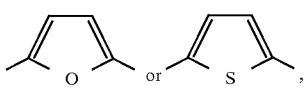

$R_2$, $R_3$, $R_4$ and $R_5$ are each independently of one another hydrogen, chloro, hydroxy, $C_1$–$C_{25}$alkyl, $C_7$–$C_9$-phenylalkyl, unsubstituted or $C_1$–$C_4$alkyl-substituted phenyl, unsubstituted or $C_1$–$C_4$alkyl-substituted $C_5$–$C_8$cycloalkyl; $C_1$–$C_{18}$alkoxy, $C_1$–$C_{18}$alkylthio, $C_1$–$C_4$alkylamino, di-($C_1$–$C_4$alkyl)amino, $C_1$–$C_{25}$alkanoyloxy, $C_1$–$C_{25}$alkanoylamino, $C_3$–$C_{25}$alkenoyloxy, $C_3$–$C_{25}$alkanoyloxy which is interrupted by oxygen, sulfur or >N—$R_6$; $C_6$–$C_9$cycloalkylcarbonyloxy, benzoyloxy or $C_1$–$C_{12}$alkyl-substituted benzoyloxy; or each of the substituent pairs $R_2$ and $R_3$ or $R_3$ and $R_4$ or $R_4$ and $R_5$, together with the linking carbon atoms, forms a benzene ring; $R_4$ is additionally —$(CH_2)_p$—$COR_9$ or —$(CH_2)_q OH$, or, if $R_3$ and $R_5$ are hydrogen, $R_4$ is additionally a radical of formula II

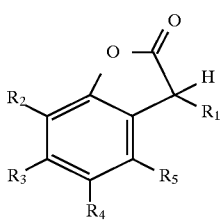

(II)

$R_6$ is hydrogen or $C_1$–$C_8$alkyl, $R_7$ is hydrogen or $C_1$–$C_8$alkyl, $R_8$ is a direct bond, $C_1$–$C_{18}$alkylene, $C_2$–$C_{18}$alkylene which is interrupted by oxygen, sulfur or >N—$R_6$; $C_2$–$C_{18}$alkenylene, $C_2$–$C_{20}$alkylidene, $C_7$–$C_{20}$phenylalkylidene, $C_5$–$C_8$cycloalkylene, $C_7$–$C_8$bicycloalkylene, unsubstituted or $C_1$–$C_4$alkyl-substituted phenylene, $R_9$ is hydroxy,

$C_1$–$C_{18}$alkoxy or

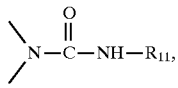

$R_{10}$ is oxygen, —NH— or

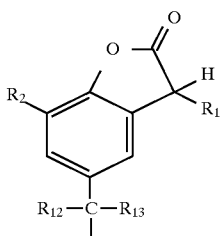

$R_{11}$ is $C_1$–$C_{18}$alkyl or phenyl, $R_{12}$ and $R_{13}$ are each independently of the other hydrogen, $CF_3$, $C_1$–$C_{12}$alkyl or phenyl, or $R_{12}$ and $R_{13}$, together with the linking carbon atom, form a $C_5$–$C_8$cycloalkylidene ring which is unsubstituted or substituted by 1 to 3 $C_1$–$C_4$alkyl groups, $R_{14}$ and $R_{15}$ are each independently of the other hydrogen, or $C_1$–$C_{18}$alkyl, M is a metal cation of valency r, n is 0, 1 or 2, p is 0, 1 or 2, q is 1, 2, 3, 4, 5 or 6, and r is 1, 2 or 3.

2. A process for the preparation of a compound of formula I

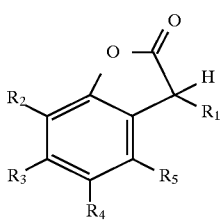  (I)

wherein $R_1$ is halogen or —$OR'_1$, $R'_1$ is hydrogen, $C_1$–$C_{25}$alkanoyl, $C_3$–$C_{25}$alkenoyl, $C_3$–$C_{25}$alkanoyl which is interrupted by oxygen, sulfur or >N—$R_6$; $C_6$–$C_9$cycloalkylcarbonyl, thenoyl, furoyl, benzoyl or $C_1$–$C_{12}$alkyl-substituted benzoyl; naphthoyl or $C_1$–$C_{12}$alkyl-substituted naphthoyl; $C_1$–$C_{25}$alkanesulfonyl, fluoro-substituted $C_1$–$C_{25}$alkanesulfonyl; phenylsulfonyl or $C_1$–$C_{12}$alkyl-substituted phenylsulfonyl;

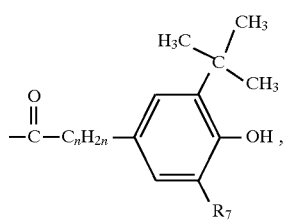

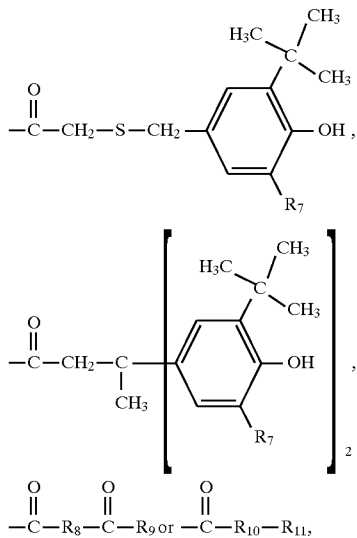

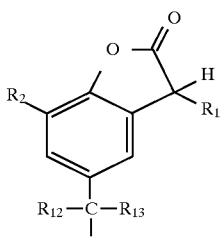

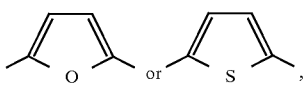

$R_2$, $R_3$, $R_4$ and $R_5$ are each independently of one another hydrogen, chloro, hydroxy, $C_1$–$C_{25}$alkyl, $C_7$–$C_9$-phenylalkyl, unsubstituted or $C_1$–$C_4$alkyl-substituted phenyl, unsubstituted or $C_1$–$C_4$alkyl-substituted $C_5$–$C_8$cycloalkyl; $C_1$–$C_{18}$alkoxy, $C_1$–$C_{18}$alkylthio, $C_1$–$C_4$alkylamino, di-($C_1$–$C_4$alkyl)amino, $C_1$–$C_{25}$alkanoyloxy, $C_1$–$C_{25}$alkanoylamino, $C_3$–$C_{25}$alkenoyloxy, $C_3$–$C_{25}$alkanoyloxy which is interrupted by oxygen, sulfur or >N—$R_6$; $C_6$–$C_9$cycloalkylcarbonyloxy, benzoyloxy or $C_1$–$C_{12}$alkyl-substituted benzoyloxy; or each of the substituent pairs $R_2$ and $R_3$ or $R_3$ and $R_4$ or $R_4$ and $R_5$, together with the linking carbon atoms, forms a benzene ring; $R_4$ is additionally —$(CH_2)_p$—$COR_9$ or —$(CH_2)_q$OH, or, if $R_3$ and $R_5$ are hydrogen, $R_4$ is additionally a radical of formula II

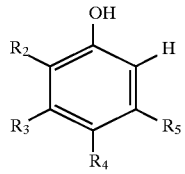

$R_6$ is hydrogen or $C_1$–$C_8$alkyl,
$R_7$ is hydrogen or $C_1$–$C_8$alkyl,
$R_8$ is a direct bond, $C_1$–$C_{18}$alkylene, $C_2$–$C_{18}$alkylene which is interrupted by oxygen, sulfur or >N—$R_6$; $C_2$–$C_{18}$alkenylene, $C_2$–$C_{20}$alkylidene, $C_7$–$C_{20}$phenylalkylidene, $C_5$–$C_8$cycloalkylene, $C_7$–$C_8$bicycloalkylene, unsubstituted or $C_1$–$C_4$alkyl-substituted phenylene,

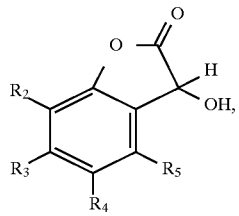

$R_9$ is hydroxy,

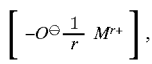

$C_1$–$C_{18}$alkoxy or

$R_{10}$ is oxygen, —NH— or

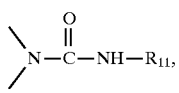

$R_{11}$ is $C_1$–$C_{18}$alkyl or phenyl,
$R_{12}$ and $R_{13}$ are each independently of the other hydrogen, $CF_3$, $C_1$–$C_{12}$alkyl or phenyl, or $R_{12}$ and $R_{13}$, together with the linking carbon atom, form a $C_5$–$C_8$cycloalkylidene ring which is unsubstituted or substituted by 1 to 3 $C_1$–$C_4$alkyl groups,
$R_{14}$ and $R_{15}$ are each independently of the other hydrogen, or $C_1$–$C_{18}$alkyl,
M is a metal cation of valency r,
n is 0, 1 or 2,
p is 0, 1 or 2,
q is 1, 2, 3, 4, 5 or 6, and
r is 1, 2 or 3;
which comprises reacting
a) one equivalent of a phenol of formula III $$\text{(III)}$$

wherein $R_2$, $R_3$, $R_4$ and $R_5$ are as defined for formula I, with 0.8 to 2.0 equivalents of glyoxylic acid, to give a compound of formula IV $$\text{(IV)}$$

(IV), and further,
b), when R'$_1$ is not hydrogen, to prepare a compound of formula I, by reacting the resultant compound of formula IV with a reactant selected from the group consisting of a hydrohalic acid, a halide of an oxysulfuric acid, a halide of phosphoric acid, a halide of phosphorous acid, an acid of formula V $$R'_1\text{—OH} \qquad \text{(V),}$$

an acid halide of formula VI $$R'_1-Y \quad (VI),$$

an ester of formula VII $$R'_1-O-R_{16} \quad (VII),$$

a symmetrical or unsymmetrical anhydride of formula VIII $$R'_1-O-R'_1 \quad (VIII),$$

or an isocyanate of formula IX $$R_{11}-N=C=O \quad (IX),$$

wherein $R'_1$ and $R_{11}$ in the compounds of formulae V, VI, VII, VIII and IX are as defined above, with the proviso that $R'_1$ is not hydrogen;

$R_{16}$ is $C_1$–$C_8$alkyl, and

Y is fluoro, chloro, bromo or iodo.

3. A process according to claim 2, wherein the glyoxylic acid is used as 40 to 60% aqueous glyoxylic acid.

4. A process according to claim 3 wherein the glyoxylic acid is 50% aqueous glyoxylic acid.

* * * * *